US011860147B2

(12) United States Patent
Rallo

(10) Patent No.: US 11,860,147 B2
(45) Date of Patent: Jan. 2, 2024

(54) SYSTEM FOR THE DETERMINATION OF THE REAL EVAPOTRANSPIRATION OF A VEGETATED SURFACE

(71) Applicant: UNIVERSITA' DI PISA, Pisa (IT)

(72) Inventor: Giovanni Rallo, Pisa (IT)

(73) Assignee: UNIVERSITA' DI PISA, Pisa (IT)

( * ) Notice: Subject to any disclaimer, the term of this patent is extended or adjusted under 35 U.S.C. 154(b) by 488 days.

(21) Appl. No.: 17/253,790

(22) PCT Filed: Jun. 19, 2019

(86) PCT No.: PCT/IB2019/055142
§ 371 (c)(1),
(2) Date: Dec. 18, 2020

(87) PCT Pub. No.: WO2019/244057
PCT Pub. Date: Dec. 26, 2019

(65) Prior Publication Data
US 2021/0123900 A1    Apr. 29, 2021

(30) Foreign Application Priority Data

Jun. 20, 2018 (IT) .......................... 102018000006477

(51) Int. Cl.
*G01N 33/24* (2006.01)
(52) U.S. Cl.
CPC ..... *G01N 33/246* (2013.01); *G01N 2033/245* (2013.01)

(58) Field of Classification Search
CPC . G01N 33/246; G01N 33/24; G01N 2033/245
See application file for complete search history.

(56) References Cited

U.S. PATENT DOCUMENTS

| 2008/0202219 A1* | 8/2008 | Schmidt | A01G 25/167 73/64.48 |
| 2010/0212409 A1 | 8/2010 | Ranjan | |
| 2021/0190743 A1* | 6/2021 | Orihara | G01N 21/78 |

FOREIGN PATENT DOCUMENTS

CN         101598587 A    12/2009

OTHER PUBLICATIONS

International Search Report and Written Opinion for International Patent Application No. PCT/IB2019/055142, dated Aug. 28, 2019, 9 pages.

(Continued)

*Primary Examiner* — Suman K Nath
(74) *Attorney, Agent, or Firm* — Armstrong Teasdale LLP

(57) ABSTRACT

A device for determining the real evapotranspiration of a vegetated surface of a soil includes a porous evaporator, at least one portion of which has resistance to water vapor flow depending on a parameter, the porous evaporator having an upper surface exposed to the atmosphere, a tank of liquid water underlying the porous evaporator to which the tank is connected by a suction tube, and provided with a meter for measuring water level, a sensor for measuring the humidity value of the soil, and a CPU controlling the parameter on which the resistance to the water vapor flow through the porous evaporator depends, depending on the humidity value of the soil detected by the sensor.

11 Claims, 1 Drawing Sheet

(56) References Cited

OTHER PUBLICATIONS

Seiko Osozawa et al., Improved Evaporimeter for Measuring Potential Evaporation from Field Soils, Soil Science and Plant Nutrition, Dec. 1987, pp. 531-538, vol. 33, No. 4, JSSSPN.

Charly Azra et al., Effect of polymer nanofibers thermoelasticity on deformable fluid-saturated porous membrane, Polymer, Feb. 10, 2015, pp. 162-169, vol. 58, Elsevier Ltd.

S. Mondal & J. L. Hu, Segmented shape memory polyurethane and its water vapor transport properties, Designed Monomers and Polymers, 2006, pp. 527-550, vol. 9, Issue 6, VSP.

* cited by examiner

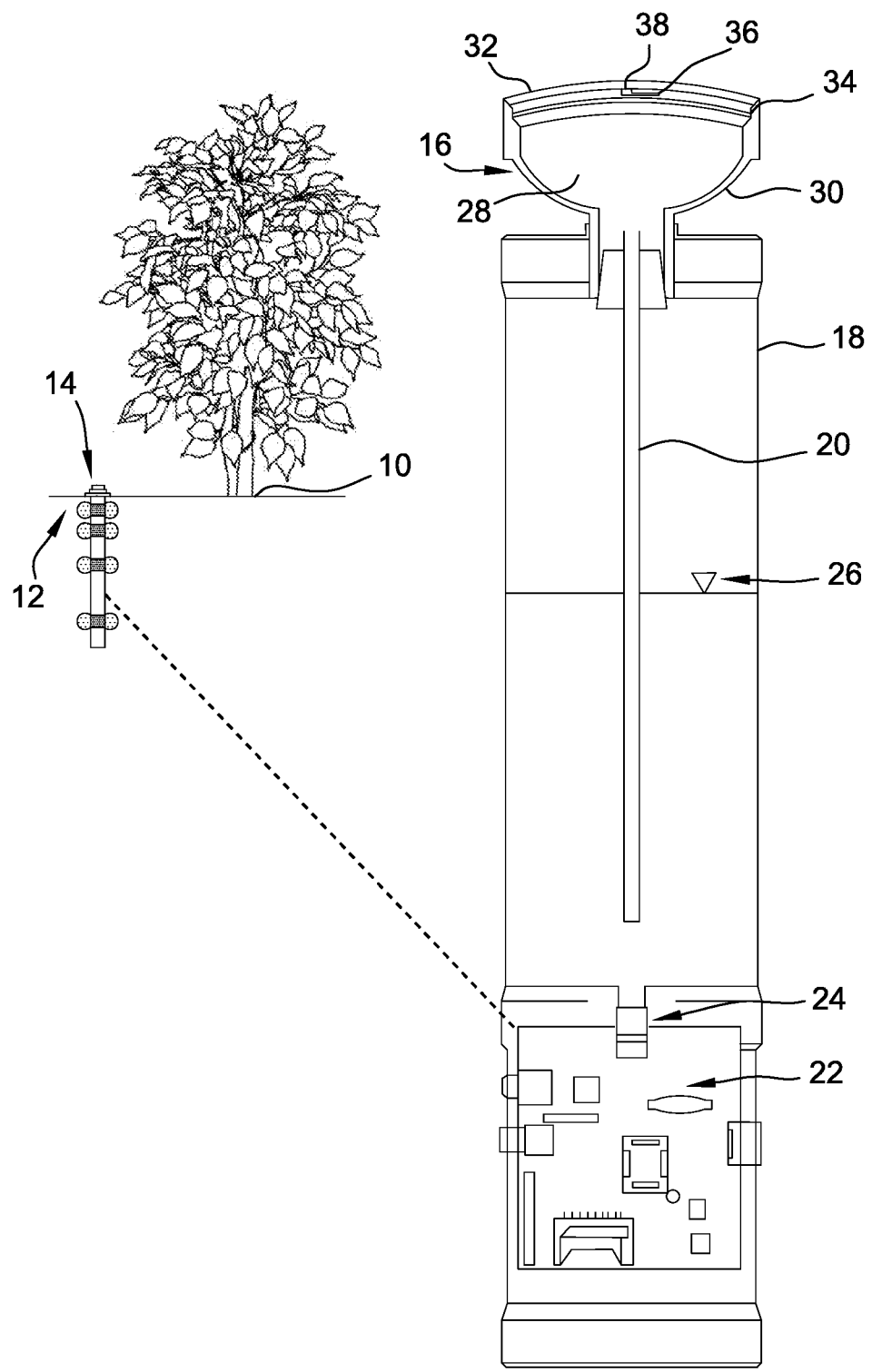

SYSTEM FOR THE DETERMINATION OF THE REAL EVAPOTRANSPIRATION OF A VEGETATED SURFACE

CROSS-REFERENCE TO RELATED APPLICATIONS

This application is a National Stage Application of International Patent Application No. PCT/IB2019/055142, having an International Filing Date of Jun. 19, 2019, which claims the benefit of priority to Italian Patent Application No. 102018000006477, filed Jun. 20, 2018, the entire contents of which are hereby incorporated by reference herein.

FIELD OF THE INVENTION

The present invention relates to a device for determining the real evapotranspiration ($ET_r$) of a natural or cultivated vegetated surface.

BACKGROUND OF THE INVENTION

A known system for determining evapotranspiration involves the use of an atmometer comprising an element that simulates vegetation, consisting of a double fabric permeable to vapor and impermeable to water in the liquid state and interposed between a porous plate which simulates a soil constantly irrigated and the atmosphere. This fabric constitutes a rigid porous medium with fixed permeance to the water vapor and analogous to the maximum stomatal one of the plants that constitutes the reference lawn.

Such a system then calculates the $ET_0$, or the reference evapotranspiration from which the $ET_r$ can be traced back using tabulated crop coefficients, appropriately adjusted to take into account the different conditions of air humidity and windiness with respect to the area where the tabulated values have been obtained experimentally. The use of additional adjustment coefficients is necessary when the water conditions of soil are different from the potential ones. The determination is therefore rather laborious and subject to inaccuracies due to the wide use of empirical coefficients.

Furthermore, systems are known which measure the water exchanges of a vegetated surface by using micrometeorological technologies, namely "eddy covariance" towers and scintillometers.

US 2010/212 409 A1 describes an atmometer comprising an evaporator having an upper surface exposed to the atmosphere, a liquid water tank provided with a level meter and underlying the evaporator to which it is connected by a suction tube, a measurement sensor of the soil humidity value, and a CPU which controls the flow of water vapor through the evaporator depending on the soil humidity value.

SUMMARY OF THE INVENTION

An object of the present invention is to provide a device for determining the real evapotranspiration of the vegetated surface of a soil, improved with respect to those described by the prior art.

According to the invention, this object is achieved with a device comprising:
- a composite porous evaporator, at least a portion of which has a resistance to the flow of water vapor that depends on a parameter, said evaporator having an upper surface exposed to the atmosphere,
- a tank of liquid water underlying the evaporator to which it is connected by a suction tube, and provided with a level meter,
- a sensor for measuring the soil humidity, and
- a central processing unit (CPU) which is configured to control said parameter on which the resistance to the flow of water vapor through the evaporator depends, in dependence on the humidity value of the soil detected by said sensor.

Preferred features of the device of the present invention are also described.

A further object of the present invention is a method for determining the real evapotranspiration by using the aforementioned device.

An essential aspect of the device of the invention is the ability to vary the resistance, that is, its inverse, i.e. the permeance, to the flow of water vapor through the evaporator depending on the water state of the soil. In this way, the flow of water vapor coming out of the device, which is calculated starting from the decrease in the level of water in the tank, constitutes a very reliable approximation of the real evapotranspiration of the vegetated surface of the soil, which depends on its water state, in addition to the atmospheric conditions to which the upper surface of the evaporator is exposed similarly to the soil.

Typically, the controlled parameter on which the resistance/permeance to the water vapor flow through the evaporator depend is the temperature, which in turn is preferably regulated by the generation of heat by a resistor forming part of an electrical circuit inserted in the evaporator and controlled by the CPU.

Other parameters that can be controlled alternatively or in addition to the temperature are of a geometric nature, such as for example the thickness of the evaporator and/or the presence of gaps between the constitutive layers thereof.

The device and the process of the invention, which are based on real measurements, therefore have the advantage of minimizing, if not canceling, the use of tabulated crop coefficients, which must be subsequently corrected.

The device of the invention is also less cumbersome and expensive, as well as simpler from the point of view of the electrical and computational scheme, than known systems based on micrometeorological technologies.

BRIEF DESCRIPTION OF THE FIGURE

Further advantages and features of the present invention will become apparent from the following detailed description, given by of a non-limiting example with reference to the accompanying drawing, in which:

FIG. 1 is a schematic representation of a device of the invention.

DETAILED DESCRIPTION

A device for determining the real evapotranspiration of a vegetated surface 10 of a soil 12, comprises a sensor 14 for measuring the humidity of the soil 12, a porous evaporator 16, a tank 18 of liquid water underlying the evaporator 16 to which it is connected by a suction tube 20, and a control CPU 22.

The tank 18 kept in depression to allow the water to rise through the tube 20 towards the evaporator 16, is provided with a water level meter 24, the measured values whereby are transmitted to the CPU 22.

The evaporator 16 has a composite structure comprising a lower plate 28 of ceramic material enclosed by a waterproofed ceramic capsule 30, an upper layer 32 of fabric exposed to the atmosphere and having a color and albedo corresponding to those of the vegetated surface, and an intermediate layer 34 having resistance to the water vapor flow which depends on the temperature parameter.

Preferably, the upper layer 32 is Green Canvas acrylic fabric produced by Sunbrella Fabrics (1831 N. Park Avenue Glen Raven, NC, USA), green Erin color and albedo of about 0.2.

Advantageously, the intermediate layer 34 is of a fabric which incorporates shape memory polymeric material which varies its geometry following the variation of a thermal parameter such as temperature. Preferably, such shape memory polymeric material is poly-NiPAAm/chitosan microgel.

In the intermediate layer 34 a resistor 36 is embedded which is part of an electrical circuit (not shown in the diagram of FIG. 1) and whose heat generation is controlled by the CPU 22 on the basis of the temperature values of the intermediate layer 34 detected by a sensor, such as a thermocouple 38.

A process for determining the real evapotranspiration of the vegetated soil surface by using the aforementioned device installed therein is now described.

Liquid water previously fed into the tank 18 is suctioned through the tube 20 into the evaporator 16. Crossing the latter, the water vaporizes and finally passes into the atmosphere exiting from the upper layer 32. Thanks to the level measurements 26 performed by the meter 24, the CPU 22 is able to calculate the decrease in the quantity of water present in the tank 18, which corresponds to the vaporized quantity. The CPU 22 is also able to control the resistance, or rather its inverse, i.e. the permeance, to the vapor flow of the intermediate layer 34 of the evaporator 16 depending on the humidity value of the soil 12 measured by the sensor 14, in a manner such that the calculated flow of vaporized water, or the quantity of vapor flowing in the unit of time through the surface unit, substantially corresponds to the flow of evapotranspiration which actually takes place through the vegetated surface 10 of the soil 12 and which is therefore estimated by the device in a suitably accurate manner.

In particular, the more the soil 12 is wet, the more the resistance to the vapor flow of the evaporator 16 is decreased, while the more the soil 12 is dry the more the resistance to the vapor flow of the evaporator 16 is increased.

For this purpose, the fact that the resistance/permeance to the water vapor flow of the intermediate layer 34 of the evaporator 16 depends on its temperature is exploited. Therefore, the CPU 22 controls the latter parameter, so as to cause the evaporator 16 to assume the desired value of resistance/permeance to the vapor flow at a given rate of humidity of the soil 12.

Specifically, the temperature is controlled by the CPU 22 by regulating the generation of heat by the resistor 36 based on the temperature values detected by the thermocouple 38, according to well-known principles of system thermal regulation. For example, if the detected temperature is lower than the desired one, heat generation is increased by increasing the intensity of electric current flowing through the resistor and/or the resistance of the latter, or vice versa, so as to compensate for the deviation of the temperature parameter from the desired value.

Of course, the principle of the invention being unchanged, the details of construction and the embodiments may widely vary with respect to what has been described purely by way of example, without thereby departing from the scope of the invention as defined in the appended claims.

In particular, any "thermally-driven" fabric could be used as constitutive of the intermediate layer of the evaporator, in which the temperature induced through a thermo-resistor causes the permeance to vary due to the vapor flow as it exceeds the so-called activation temperature of the constitutive shape-memory polymers. Also porous membranes based on nano-polyurethane fibers sensitive to thermal stimuli belong to this category of fabrics, which are inserted through electrospinning and laid therein (Charly Azra et al., 2015: Mondal et al., 2006). Such polymers in particular have a permeability to water vapor variable in a representative domain of the main agricultural crops, and in particular $<1000$ $g*m^{-2}*d^{-1}$, which corresponds to a stomatal resistance of about 100 $s*m^{-1}$.

It is also possible to use as constitutive materials of the intermediate layer of the evaporator polymers which can be activated through low-power electrical stimuli, thus avoiding the generation of heat and the consequent alteration of the heat balance in the area of the device affected by the water exchange process: in fact, one thermal stimulus, different from the environmental one, modifies the water state and therefore the natural vapor concentration gradient of the system.

Such a stimulus is for example represented by a voltage difference which does not cause the material to heat up, but causes its porosity to vary in combination with the thickness of the material itself. A combined variation of porosity and thickness results in a variation of the tortuosity, much more effective than the variation of porosity alone in order to influence the resistance to the water vapor flow.

Furthermore, the controlled creation of a gap between the porous plate and the intermediate layer of the evaporator allows controlling the global permeance of the device also through this way.

For this purpose, graphene actuators or actuators based on polythiophene gels capable of converting an electrical stimulus into mechanical energy can be used, so as to generate a gap between the porous plate and the intermediate layer of the evaporator, varying the resistance to the water vapor flow.

What is claimed is:

1. A device for determining the real evapotranspiration of a vegetated surface of a soil, the device comprising:
    a porous evaporator, at least one portion of which has resistance to a water vapor flow depending on a parameter of the porous evaporator, the porous evaporator having an upper surface exposed to the atmosphere,
    a tank of liquid water underlying said porous evaporator to which said tank is connected by a suction tube, and provided with a meter for measuring water level,
    a sensor for measuring a soil humidity value, and
    a CPU that controls said parameter on which the resistance to the water vapor flow through said porous evaporator depends, in dependence on the soil humidity value detected by said sensor.

2. The device of claim 1, wherein said porous evaporator comprises a lower plate of ceramic material, an upper layer of fabric exposed to the atmosphere, and an intermediate layer having resistance to the water vapor flow depending on said parameter, said parameter including temperature, and wherein a resistor is embedded, said resistor being part of an electric circuit controlled by said CPU that establishes, by heat generation of said resistor, said temperature parameter of said porous evaporator, and consequently the water vapor flow that passes through it, in dependence on the soil humidity value detected by said sensor.

3. The device of claim 2, wherein said intermediate layer is made of a fabric incorporating a shape-memory polymeric material that varies its geometry as a result of a variation in temperature.

4. The device of claim 3, wherein said shape memory polymeric material is a poly-NiPAAm/chitosan microgel.

5. The device of claim 1, wherein said upper surface of said porous evaporator has color and albedo similar to those of the vegetated surface.

6. The device of claim 1, wherein said parameter is the temperature of said porous evaporator.

7. The device of claim 6, wherein a thermocouple detects a temperature value of said porous evaporator, and transmits it to said CPU.

8. A method for determining the real evapotranspiration of a vegetated surface of a soil by a device, the method comprising:
- a porous evaporator, at least one portion of which has resistance to a water vapor flow depending on a parameter of the porous evaporator, the porous evaporator having an upper surface exposed to the atmosphere,
- a tank of liquid water underlying the porous evaporator to which the tank is connected by a suction tube, and provided with a meter for measuring water level,
- a sensor for measuring a soil humidity value, and
- a CPU that controls the parameter on which the resistance to the water vapor flow through the porous evaporator depends, in dependence on the soil humidity value detected by the sensor,
- wherein evapotranspiration is calculated by the CPU from a decrease in the water level in the tank detected by the meter, the decrease being an index of the water vapor flow through the porous evaporator.

9. The method of claim 8, wherein the parameter is the temperature of the porous evaporator.

10. The method of claim 9, wherein the temperature of the porous evaporator is established by heat generation of a resistor embedded in the porous evaporator and being part of an electric circuit controlled by the CPU.

11. The method of claim 10, wherein a control action of the CPU takes place on the basis of temperature values of the porous evaporator detected by a thermocouple.

* * * * *